United States Patent
Kwon et al.

(10) Patent No.: US 9,781,899 B2
(45) Date of Patent: Oct. 10, 2017

(54) *PLEUROTUS ERYNGII* VAR. *FERULAE* STRAIN

(71) Applicant: Kyong Yeal Kwon, Chungcheongnam-do (KR)

(72) Inventors: Kyong Yeal Kwon, Chungcheongnam-do (KR); Seong Jin Lee, Chungcheongnam-do (KR); Ook Jin Jeong, Chungcheongnam-do (KR); Ki Moon Park, Gyeonggi-do (KR); Jae Young Rho, Chungcheongnam-do (KR)

(73) Assignee: Kyong Yeal Kwon, Chungcheongnam-Do (KR)

( * ) Notice: Subject to any disclaimer, the term of this patent is extended or adjusted under 35 U.S.C. 154(b) by 375 days.

(21) Appl. No.: 14/415,593

(22) PCT Filed: Jul. 16, 2013

(86) PCT No.: PCT/KR2013/006366
§ 371 (c)(1),
(2) Date: Jan. 18, 2015

(87) PCT Pub. No.: WO2014/014258
PCT Pub. Date: Jan. 23, 2014

(65) Prior Publication Data
US 2015/0208604 A1    Jul. 30, 2015

(30) Foreign Application Priority Data

Jul. 17, 2012    (KR) .................. 10-2012-0077987

(51) Int. Cl.
*A01H 15/00*    (2006.01)
*C12N 1/14*    (2006.01)

(52) U.S. Cl.
CPC .............. *A01H 15/00* (2013.01); *C12N 1/14* (2013.01)

(58) Field of Classification Search
None
See application file for complete search history.

(56) References Cited

FOREIGN PATENT DOCUMENTS

| JP | 2007-37455 A | 2/2007 |
| JP | 2007-53928 A | 3/2007 |
| KR | 10-0395423 B1 | 8/2003 |
| KR | 10-0954964 B1 | 4/2010 |

OTHER PUBLICATIONS

De Gioia et al 2005 Mycological Research 109(1): 71-80.*
International Search Report for PCT/KR2013/006366, dated Nov. 29, 2013.
Office action from Korean Intellectual Property Office in a counterpart Korean patent application (The listed reference is cited in this IDS.), dated 2014.
Jae-Sun Choi et al., Genetic Relationship of Pleurotus ferulae Strains, Korean Journal of Mycology, 37(1): 28-32 (2009).
Zhang, J. X. et al., Genetic polymorphism of *Ferula* mushroom growing on *Ferula sinkiangensis*., Appl. Microbiol. Biotechnol. 71(3): 304-309 (Oct. 1, 2005).

* cited by examiner

*Primary Examiner* — David H Kruse
(74) *Attorney, Agent, or Firm* — The PL Law Group, PLLC

(57) ABSTRACT

The present invention relates to *Pleurotus eryngii* var. *ferulae*. More particularly, the present invention relates to a novel *Pleurotus eryngii* var. *ferulae* strain line following a line of DDL01 (KACC93085P) which is obtained by selecting a conventionally known *Pleurotus eryngii* var. *ferulae* strain and then cross-breeding the selected strain with the *Pleurotus eryngii* var. *ferulae* strain DDL01 (accession number: KACC93085P), and also relates to a fruit body obtained through cultivation of the strain.

7 Claims, 4 Drawing Sheets

PLEUROTUS ERYNGII VAR. FERULAE STRAIN

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/006366, filed Jul. 16, 2013, which claims priority to Korean Patent Application No. 10-2012-0077987, filed Jul. 17, 2012, entire contents of which are incorporated herein by reference.

TECHNICAL FIELD

The present invention relates to a variant of *Pleurotus eryngii*. More particularly, the present invention relates to a novel strain of *Pleurotus eryngii* var. *ferulae*, which is a descendant of the *Pleurotus eryngii* strain DDL01 (Accession No.: KACC93085P), created by crossbreeding the *Pleurotus eryngii* strain DDL01 (KACC93085P) with a *Pleurotus eryngii* strain selected from known species, and a fruit body obtained from the strain.

BACKGROUND ART

*Pleurotus eryngii* var. *ferulae* is taxonomically controversial because it may belong to a variety of *Pleurotus eryngii* or may be classified as an independent species (*Pleurotus ferulae*) of the *Pleurotus* genus in the Pleurototaceae family. The mushroom is edible, and is known by various names in many countries.

In 1958, artificial cultivation of *Pleurotus eryngii* var. *ferulae* started in many countries including India, France, and Germany, and was first achieved by Kalmer. The mushroom was successfully cultured with sawdust, cottonseed husk, and wheat bran in 1983 in China. Superior strains were acquired by monospore crossbreeding in 1990, and were widely used in Fujian province, and Xinjiang province of China (Lee Dong-hee, 2005). The annual output of mushroom was only approximately 1,000 tons worldwide (Hong Ki-young, 2004).

With regard to morphological features of fruit bodies of *Pleurotus eryngii* var. *ferulae*, their pileus is 15-100 mm in size with the optimum size being 20-50 mm. Initially, the pileus is hemispherical and has an edge that is internally rolled. When fully grown, the pileus spreads semi-hemispherically, flat with a slightly recessed center, or flat. A hemispherical pileus is considered optimal. Its surface is smooth. When young, the pileus takes a brownish grey color (5D2, Methuen Handbook of Color), which turns grayish orange (5B3) as the mushroom matures. The pileus absorbs water under wet conditions, but becomes hygrophanous in a dry environment. The flesh of *Pleurotus eryngii* var. *ferulae* is white and has a smooth and elastic texture. It tastes sweet, with a flavor similar to that of sugar cane. Particularly when chewed, the mushroom provides a good crunch sensation. The gill is decurrent against the stipe, and of tetrabranch type with a dimension of 15-35×1-3 mm, and is slightly densely populated. At an initial stage, the gill is ivory white, which turns yellowish white (4A2) as the mushroom grows. Each gill blade is wide and flat. The stipe has a size range of 50-150×15-35 mm, with preference for a cylindrical morphology with a size of 15-40×70-90 mm. It becomes somewhat thicker or expands towards the ground side. Its surface is ivory white, and has a smooth surface. The stipe is closely packed, with high solidity in the longitudinal direction, but can be torn thinly in the latitudinal direction. The spore is white, and cylindrical with a dimension of 5~6×7~9 µm. The basidium has a long club shape with a size of 24-39×5-7 µm. Most basidia are of tetraspore type, with a clamp at the aerial part thereof. As for the cheilocystidia, its morphology is a club, a spindle, or a club-like spindle, with a size of 25-35×5-8 µm. Generally, it has a 1-3 pin-like protrusions at the top, and its cell wall is thin and transparent. There are no pleurocystidia. The fruit body is of a monomitic tissue type with a parallel-interwoven texture, and there is a clamp in the septum of the hyphae

*Pleurotus eryngii* var. *ferulae*, exhibiting these morphological features, is richer in flavor and of higher edibility value, compared to other mushrooms, and is known to exert anti-tumor and antidiabetic activity (Hong, at al., 2004). Also, the mushroom has been shown to have medicinal effects on the prevention of gastric and renal disorders, cough, inflammation, and obstetric and gynecological diseases (KIM Dae Sik, 2002). Abundant in dietary fiber, amino acids, and minerals, *Pleurotus eryngii* var. *ferulae* is valuable as a health food and as a functional mushroom. In Japan, *Pleurotus eryngii* var. *ferulae* has recently attracted interest as an edible mushroom and sharply increased in production. In Korea, the mushroom has been studied from 2001, but failed in terms of commercialization until the development of *Pleurotus eryngii* var. *ferulae* DDL01 (accession No.: KACC93085P) by the present inventor in late 2009. The mushroom is now commercially available.

Because of its good taste and morphology as well as short cultivation period, *Pleurotus eryngii* var. *ferulae* DDL01 (accession No.: KACC93085P) is of high commercial value. Also, it can be cultured in a bottle. By virtue of these advantages, the mushroom is commercialized in Japan and the U.S.A. as well as in Korea.

However, consumers in the U.S.A. show a preference for this mushroom when the pileus of its fruit body is closer to white in colour. To create a higher additional value in the U.S.A., the greatest market in the world, *Pleurotus eryngii* var. *ferulae* DDL01 needs to be modified in color or other morphological features.

SUMMARY

Leading to the present invention, intensive and thorough research, conducted by the present inventor, succeeded in culturing a novel strain that is superior to DDL01 (KACC93085P) in commercial marketability.

It is therefore an object of the present invention to provide a novel *Pleurotus eryngii* var. *ferulae* strain derived from DDL01 (KACC93085P) that has a more white pileus surface than in DDL01 (KACC93085P), thereby attracting consumer's attention, and a fruit body produced by culturing the novel strain.

It is another object of the present invention to provide a novel strain P48-24s (accession No.: KCCM11288P) derived from DDL01 (KACC93085P), which takes an ivory white color on its pileus surface, without any other colors mixed in, thus attracting consumers' attention, and a fruit body produced by culturing the novel strain.

It is a further object of the present invention to provide a *Pleurotus eryngii* var. *ferulae* strain of PS48-24 lineage, obtained by the monospore cross of the novel strain P48-24s, which does not form a confrontation line upon replacement culture at regular intervals with the novel strain P48-24s on a medium, and a fruit body produced by culturing the strain.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims.

In accordance with an aspect thereof, the present invention provides a novel *Pleurotus eryngii* var. *ferulae* strain P48-24s (accession No.: KCCM11288P). This strain was deposited at the Korean Culture Center of Microorganism on Jun. 25, 2012 (accession No.: KCCM11288P).

In one preferred exemplary embodiment, the novel strain is obtained by crossing a monospore isolated from a fruit body of the *Pleurotus eryngii* var. *ferulae* strain DDL01 (accession No.: KACC93085P) with a monospore isolated from a *Pleurotus eryngii* var. *ferulae* strain other than the *Pleurotus eryngii* var. *ferulae* strain DDL01.

In another preferred exemplary embodiment, when the novel strain is inoculated at regular intervals in a medium and subjected to replacement culture, no confrontation lines are formed on the medium.

In accordance with another aspect thereof, the present invention provides a *Pleurotus eryngii* var. *ferulae* fruit body produced by the novel *Pleurotus eryngii* var. *ferulae* strain P48-24s (accession No: KCCM11288P).

In one preferred exemplary embodiment, the fruit body has a pileus surface that is fully ivory white, without any other colors mixed therein.

In another preferred exemplary embodiment, the fruit body has a bisporous basidium.

In accordance with a further aspect thereof, the present invention provides spore isolates from the *Pleurotus eryngii* var. *ferulae* fruit body.

In accordance with a still further aspect thereof, the present invention provides a mycelial culture of the novel *Pleurotus eryngii* var. *ferulae* strain P48-24s (accession No: KCCM11288P).

In accordance with still another aspect thereof, the present invention provides an inoculum including the mycelia culture.

In accordance with yet another aspect thereof, the present invention provides a *Pleurotus eryngii* var. *ferulae* strain of P48-24s lineage, obtained by monospore crossing between the spore isolates.

In a preferred exemplary embodiment, when the novel *Pleurotus eryngii* var. *ferulae* strain P48-24s is inoculated at regular intervals in a medium and subjected to replacement culture, no confrontation lines are formed on the medium.

In accordance with a yet further aspect thereof, the present invention provides a *Pleurotus eryngii* var. *ferulae* fruit body produced by the *Pleurotus eryngii* var. *ferulae* strain of P48-24s lineage.

In accordance with a yet still further aspect thereof, the present invention provides spore isolates from the *Pleurotus eryngii* var. *ferulae* fruit body of P48-24s lineage.

In accordance with an additional aspect thereof, the present invention provides a mycelial culture of any one of the *Pleurotus eryngii* var. *ferulae* strains of P48-24s lineage.

In accordance with an additional another aspect thereof, the present invention provides an inoculum including the mycelia culture.

Advantages of the present invention are as follows.

Provided according to the present invention are a novel *Pleurotus eryngii* var. *ferulae* stain of the DDL01 (KACC93085P) strain lineage that takes a more white color on the pileus surface than does the commercialized DDL01 (KACC93085P), thus attracting consumer's attention, and a fruit body produced by culturing the strain.

In addition, both the novel *Pleurotus eryngii* var. *ferulae* strain and the fruit body take an ivory white color on the surface of pileus, without any other colors mixed therein, thus attracting consumer's attention and improving in quality and commerciality.

Further, the present invention provides a *Pleurotus eryngii* var. *ferulae* strain of PS48-24 lineage, obtained by the monospore cross of the novel strain P48-24s, which does not form a confrontation line upon replacement culture at regular intervals with the novel strain P48-24s on a medium, and a fruit body produced by culturing the strain.

DETAILED DESCRIPTION

Figure 1:
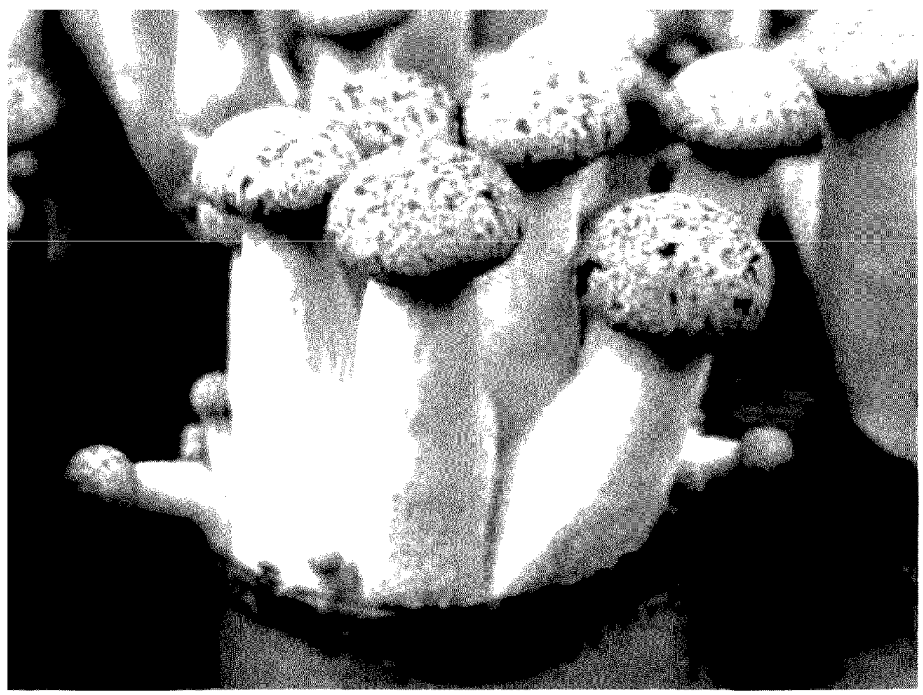
FIG. 1 is a photograph of fruit bodies of the commercialized *Pleurotus eryngii* var. *ferulae* DDL01 (KACC93085P).

Terms used herein are selected from among the terminology currently used in the art, but rarely made by the present inventor. In this case, the terms should not be understood as they are, but appreciated in the context of the description or meanings for which they are used.

To explain the technical constitution of the present invention in detail, reference should now be made to the drawings and preferred embodiments.

The embodiments are illustrative, and thus, the present invention may be practiced in other modifications. In drawings, the same reference numerals are used throughout the different drawings to designate the same or similar components.

The present invention features a the novel *Pleurotus eryngii* var. *ferulae* strain of the commercialized strain DDL01 (KACC93085P) lineage that is improved in morphological property to attract consumer's attention, and a fruit body produced by culturing the novel strain.

The fruit body produced by the novel *Pleurotus eryngii* var. *ferulae* strain of the present invention has a pileus surface that is fully ivory white and/or free of lists.

For use in generating the novel *Pleurotus eryngii* var. *ferulae* strain, DDL01 (KACC93085P), DAC7322, and DAC7421 were selected from among the strains stored in the institute attached to the company Dole-A-Che by test culturing. In the following experiments, they were used as parent strains.

Example 1: Culture of Novel *Pleurotus eryngii* Var. *Ferulae* Strain P48-24s

Of strains stored in the institute attached to the company Dole-A-Che, DDL01 (KACC93085P), DAC7322, and DAC7421 were employed as parent stains in this Example.

(1) Isolation of Monospore

After removing the stipe from each of the *Pleurotus eryngii* var. *ferulae* strains DDL01, DAC7322 and DAC7421, the pileus thus left was placed on a petri dish such that the gills faced downwards. After 24 hours, the pileus was withdrawn, and the spores dropped on the petri dish were diluted to a suitable concentration in sterilized water. The dilution was spread over a potato agar plate, followed by incubation at 25° C. Primary hyphae germinated from 7 days after incubation were isolated with tooth picks, and then were inoculated into respective potato agar plates. After incubation at 25° C. for 14 days, hyphae were partly isolated from the potato agar plates and observed under a microscope to determine the presence or absence of clamps. Only the hyphae that were observed to have no clamps were immersed in a 10% glycerol solution before cold storage.

(2) Crossing

Crossing was performed between the cold-stored monospore (monokaryotic) hyphae from the same or different *Pleurotus eryngii* var. *ferulae* strains, and between the cold-stored monospore (monokaryotic) hyphae and the hyphae (dikaryotic) of the parent strains. The hyphae were inoculated into respective potato agar plates, and cultured at 25° C. for 14 days. For use in crossing, selection was made only of the hyphae that well grew to produce high mycelial mass. The mycelia grown on the potato agar plates were cut in a size of 1 cm circle to give mycelial blocks. They were inoculated at regular intervals of 3 cm onto a potato agar plate to conduct cross breeding. After incubation of the inoculated potato agar plate at 25° C. for 21~28 days, the hyphae were observed under a microscope. Only the strains that had clamps formed in the monokaryotic mycelia blocks were selected.

(3) Culture of Crossed Strains

Sawdust was mixed at a volume ratio of 8:2 with rice bran, and adjusted to have a water content of 64%, after which the mixture was added in an amount of 580 g to each of 850 cc culture bottles. The mixture was perforated at the center from the top to the bottom, using a 2 cm bar, followed by autoclaving at 121° C. for 60 min. Thereafter, the bottles were cooled to 20° C., inoculated with the selected strains, and incubated at 24° C. for 30 days in a dark place. After completion of the incubation, mycelia were scraped and subjected to a breeding test, such as germination and breeding at 14~18° C. and at a humidity of 80~95% under 100~200 Lux.

(4) Selection of the Novel Crossed Strain *Pleurotus eryngii* Var. *Ferulae* P48~24s The strains obtained by monosporic crossing were bred and screened to select monospores P7329W, P7330W, and P7332W of DDL01(KACC93085P) featuring an ivory white color on the pileus of the fruit body. Of them, P7332W was primarily crossed with DAC7322 (dikaryotic) to give a crossed strain DAC7348. Then, crossing was performed between monospores of DAC7348 and DAC7421 to select crossed strains exhibiting ivory white pilei. Also selection was made of a crossed strain that was semi-hemispherical and took an ivory white color on the pileus of the fruit body without any other colors mixed therein. This strain was termed P48-24s, and was duly deposited at the Korean Culture Center of Microorganism (having the address of KCCM, 3F Yurim B/D, 361-221, Hongje-1-dong, Sudaemun-gu, Seoul 120-091, Republic of Korea) under the Access number of KCCM11288P on Jun. 25, 2012. The deposit has been made under the terms of the Budapest Treaty and all restrictions imposed by the depositor on the availability to the public of the biological material will be irrevocably removed upon the granting of a patent.

Example 2: Breeding of P48-24S-Lineage *Pleurotus eryngii* Var. *Ferulae* Strains 1 to 5

(1) Isolation of monospore, (2) Crossing, and (3) Culture of crossed strains were carried out in the same manner as in Example 1, with the exception that the novel strain P48-24s selected in Example 1 was used as a parent strain. Crossing the monospores from the novel strain P48-24s resulted in P48-24s lineage *Pleurotus eryngii* var. *ferulae* Strains 1 to 5, that is, P48-24S progenies 1 to 5.

Experimental Example 1: Mycological Feature of Novel Crossed Strain P48-24s and P48-24S Lineage *Pleurotus eryngii* Var. *Ferulae* Strains 1 to 5

The novel crossed strain P48-24s obtained in Example 1 and the P48-24S lineage *Pleurotus eryngii* var. *ferulae* Strains 1 to 5 obtained in Example 2 were examined for mycological feature as follows.

1) State of growth on potato dextrose agar (PDA) plate (25° C.): on day 7, colonies with a diameter of 40.7 mm. White hyphae populated densely. Aerial mycelia grew straight, with moderate mass.

2) State of growth on mushroom complete medium (MCM) (25° C.) on day 7, colonies with a diameter of 36.1 mm. White hyphae populated densely. Aerial mycelia grew straight, with moderate mass.

3) State of growth on mycological agar (MA) plates (25° C.) on 7 day, colonies with a diameter of 40.3 mm. White hyphae populated densely. Aerial mycelia grew straight, with moderate mass.

4) State of growth on corn meal agar (CMA) plate (25° C.): on day, colonies with a diameter of 39.3 mm. White hyphae populated densely. Aerial mycelia grew straight, with very small mass.

5) State of growth on sabouraud dextrose agar (SDA) plate (25° C.): on day 7, colonies with a diameter of 38.5 mm. White hyphae populated densely. Later, mycelia partly turned redish yellow. Aerial mycelia grew straight with moderate mass.

6) Optimal temperature for hyphal growth: After seed fungi was inoculated into a 5 mm hole of PDA media and incubated at different temperatures for 7 days, diameters of the colonies thus formed were measured. At around 26° C., hyphae grew optimally.

7) Optimal pH for hyphal growth: After a glucose-peptone-yeast extract broth was sterilized, and adjusted to different pH values, seed fungi were inoculated to 25 mL aliquots of the broth, and cultured in a stationary manner at 25° C. for 12 days. Dry mycelial mass was measured, indicating an optimal pH of around 5.5.

Experimental Example 2: Genetic Features of Novel Strain P48-24s, and P48-24S-Lineage *Pleurotus eryngii* Var. *Ferulae* Strains 1 to 5

Examination was made of genetic features of the strains obtained in Examples. On the ground of the mycological taxonomic fact that two hyphae are different to each other if different in fertility factor, both parents and genetically related cultivars were subjected to replacement culture on agar plates to determine whether they were different or identical in fertility factor. Two different stains were seeded at a distance of 3 cm from each other on an agar plate and cultured at 25° C. for 14~21 days, after which the formation of a confrontation line between the two colonies was observed (when a confrontation line was formed, + while no lines, −). The results are summarized in Table 1. Herein, P48-24S-Lineage *Pleurotus eryngii* var. *ferulae* strains 1 to 5 were progenies from P48-24S, obtained by crossing monospores of the novel strain P48-24S.

TABLE 1

| Strains | P48-24S | Progeny 5 from P48-24S |
|---|---|---|
| *P. nebrodensis* (China) | + | + |
| *P. nebrodensis* (Hwanghoo | + | + |
| *P. ferulae* var. *fuscus*(KCTC 26065) | + | + |
| *P. eryngii* (cultured) | + | + |
| *P. ferulae*(China) | + | + |
| *P. eryngii* var. *ferulae*(DAC 7322) | + | + |
| *P. eryngii* var. *ferulae*(DAC 7421) | + | + |
| *P. eryngii* var. *ferulae*(DDL01) | + | + |
| P48-24s | − | − |
| Progeny 1 from P48-24S | − | − |
| Progeny 2 from P48-24S | − | − |
| Progeny 3 from P48-24S | − | − |
| Progeny 4 from P48-24S | − | − |

Experimental Example 3: Molecular Biological Identification of Novel Strain P48-24s (1) Base Sequencing of ITS Region Using a bead beating method, DNA was extracted from cultivars. ITS (internal transcribed spacer) was amplified from the DNA by PCR (polymerase chain reaction) using a primer set of ITS1 (TCCGTAGGTGAACCTGCGG; SEQ ID NO: 1)/ITS4 (TCCTCCGCTTATTGATATGC; SEQ ID NO: 2). The Product was purified, and base sequenced in Macrogen (SEQ ID NO: 3).

```
> P48-24s
GGAAGGATCATTAATGAATTCACTATGGAGTTGTTGCTGGCCTCTAGGGG

CATGTGCACGCTTCACTAGTCTTTCAACCACCTGTGAACTTTTGATAGAT

CTGTGAAGTCGTCTCTCAAGTCGTTAGACTTGGTTTGCTGGGATGTAAAC

GTCTCGGTGTGACTACGCAGTCTATTTACTTATAACACCCCAAATGTATG

TCTACGAATGTCATTTAAAGGGCCTTGTGCCTATAAACCATAATACAACT

TTCAACAACGGATCTCTTGGCTCTCGCATCGATGAAGAACGCAGCGAAAT

GCGATAAGTAATGTGAATTGCAGAATTCAGTGAATCATCGAATCTTTGAA

CGCACCTTGCGCCCCTTGGTATTCCGAGGGGCATGCCTGTTTGAGTGTCA

TTAAATTCTCAAACTCACTCTGGTTTTTCCAATTGTGATGTTTGGATTGT

TGGGGGCTGCTGGCCTTGACAGGTCGGCTCCTCTTAAATGCATTAGCAGG

ACTTCTCATTGCCTCTGCGCATGATGTGATAATTATCACTCATCAATAGC

ACGCATGAATAGAGTCTGGCTCTCTAACCGTCCGCAAGGACAATTTGACA

ATTTGACCTCAAATCAGGTAGGACTACCCGCTGAACTTAAGCT
```

(2) Analysis of Genetic Features

The gene the base sequences of which were determined were modified at two portions and used to search for most similar base sequences by BLAST searching. More accurate genetic analysis was performed on them.

Figure 3:
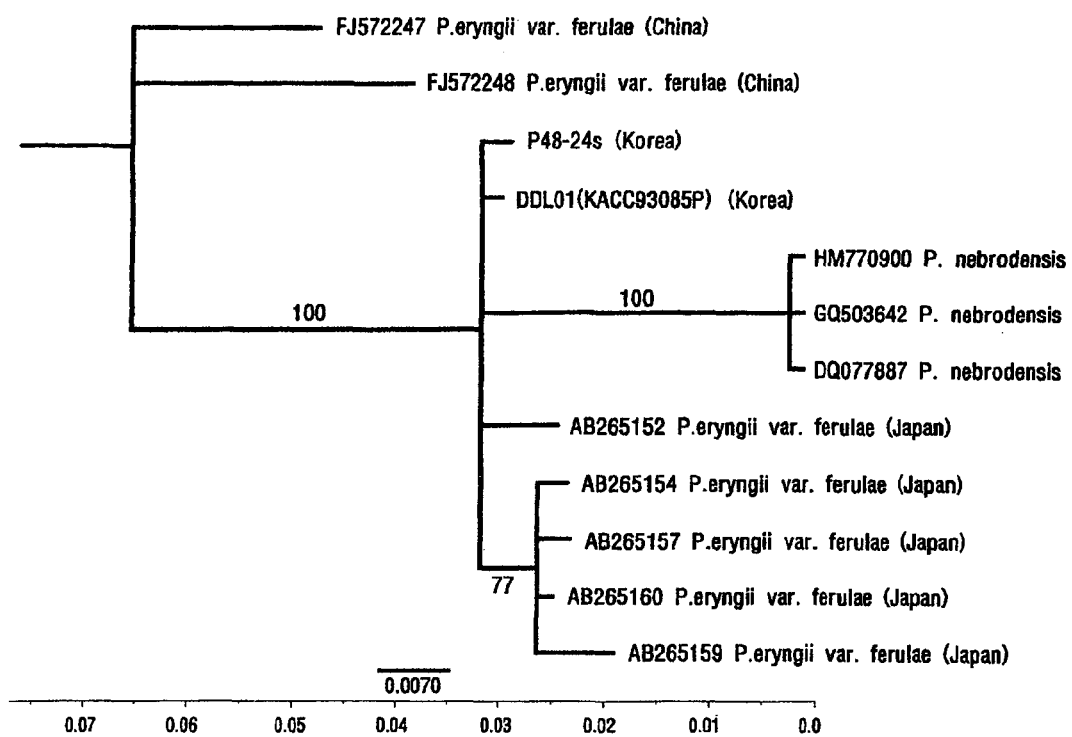
FIG. 3 is a phylogenic tree showing the novel *Pleurotus eryngii* var. *ferulae* strain P48-24s (accession No.: KCCM11288P) according to one embodiment of the present invention as classified by UPGMA.

All base sequences were aligned using ClustalW2 (Multiple Sequence Alignment). On the basis of the alignments, evolutionary distances were calculated by Bayesian MCMC run using MrBayes version 3.1 program, and molecular evolutionary relations are shown by maximum likelihood in FIG. 3. For each data set, 1000 bootstrap replicates were generated. Based on the data, they were examined for similarity and finally identified. As a result, the mushroom was identified as *Pleurotus eryngii* var. *ferulae*.

Experimental Example 4: Morphological Feature of Fruit Body of Novel Strain P48-24s

[Examination with Naked Eye]

The pileus ranges in diameter 15-90 mm, with an optimum size of 20-55 mm. Initially, the pileus is semi-hemispherical and has an edge that is internally rolled for a significant period of time. When fully matured, the pileus spreads semi-hemispherically, flat with a slightly recessed center, or flat. Its surface is pale yellowish white-ivory white, and smooth. The texture is very thick, dense, and of flesh with elasticity at the central region, but becomes thin at the edge. The pileus emanates a typical mushroom flavor, tastes sweet, and gives a good crisp chewing sensation. The gills are long and decurrent against the stipe, and are densely populated. Short gills are of mono- to tribranch type, and white at an initial stage, but turn pale grayish yellow or pale grayish orange as the mushroom grows. Each gill blade is wide and flat.

The stipe has a size of 15-55×50-150×mm (base 27 mm), with preference for a cylindrical morphology with a size of 20-40×70-90 mm. It becomes somewhat thicker towards the ground side while the aerial part becomes thin and then thick as it runs towards the top. Often, it is bent. Its surface is pale yellowish white to ivory white, has unclear longitudinal fibrous lines, and somewhat rugged, but flat. The stipe is closely packed, white, dense, and of flesh with elasticity.

[Microscopic Examination]

Spores are oval to cylinder-like oval, with a size range of 9.3-9.8×4.3-4.6 μm, and have a wide and flat surface. They are inamyloid as tested in Melzer's solution, and show an ivory white spore print.

Figure 4:
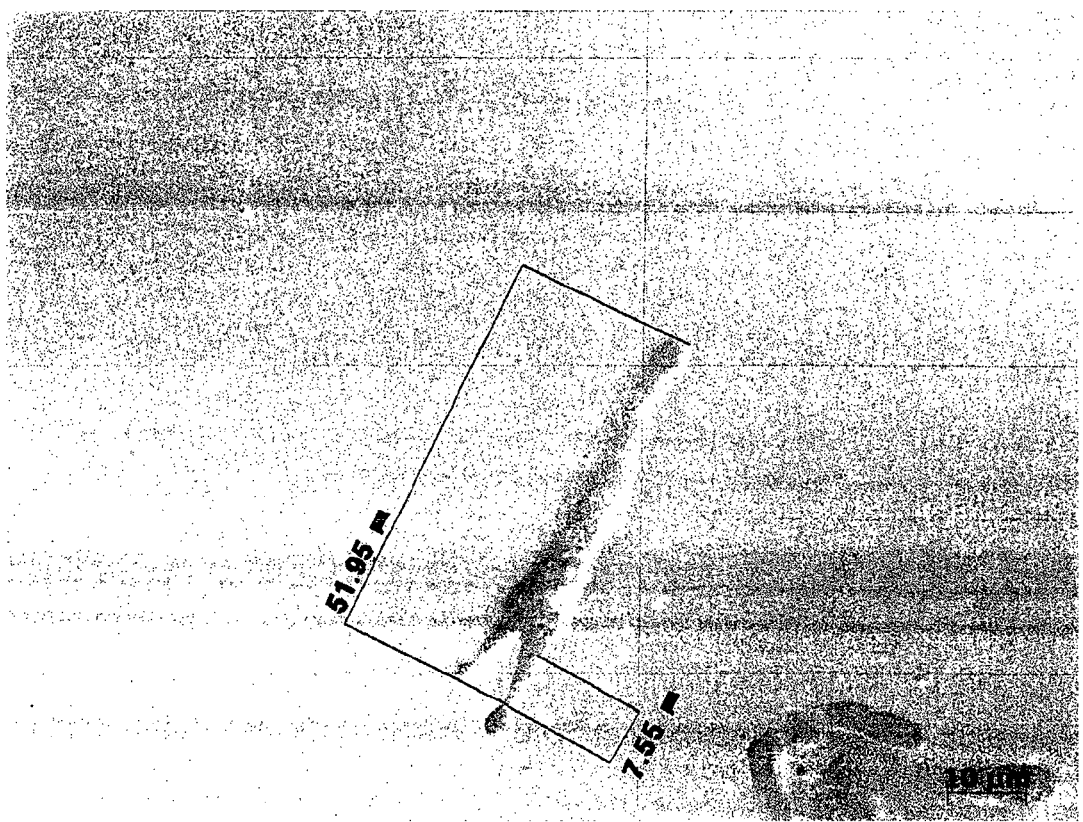
FIG. 4 is a photograph showing that the fruit body produced by the novel *Pleurotus eryngii* var. *ferulae* strain P48-24s (accession No.: KCCM11288P) according to the present invention has a bisporous basidium.

The basidium is of dibranch type. As can be seen in FIG. 4, most basidia are bisporous, and have a club-type morphology with a size range of 52-57×8.5-9 μm. Tetrasporous basidia resemble clubs, with a size range of 47-48×10-10.2 μm, and have a clamp at their base portions.

As for the cheilocystidia, its morphology is a club, a spindle, or a club-like spindle, with a size range of 25-35× 5-8 μm. Generally, it has a 1-3 pin-like protrusions at the top, and its cell wall is thin and transparent.

There are no pleurocystidia.

The fruit body is of a monomitic tissue type with a parallel-interwoven texture, and there is a clamp in the septum of the hyphae Experimental Example 5: Culture of Novel Strain P48-24s and P48-24S-Lineage *Pleurotus eryngii* Var. *Ferulae* Strains 1 to 5

1. Medium Preparation

A mixture of 8:2 of sawdust:rice bran (volume ratio, 40-50 g per 850 cc bottle) was used as a medium. Sawdust and rice bran were completely mixed by stirring, and adjusted to have a final water content of 68~70%.

2. Filling

The medium was introduced in an amount of 480-520 g into an 850 cc bottle.

3. Sterilization

Autoclaving was performed at 120° C. for 60 min (effective sterilizing time). When reference was made to the temperature of the autoclave, autoclaving was extended to 90 min (850 cc bottle).

4. Cooling

The medium was cooled to 20° C. in a clean environment.

5. Inoculation

An inoculum per bottle was about 15 cc.

6. Culturing

The culture condition was maintained at 18° C. for 25 days, and then at 23° C. for 8~10 days. Humidity was set to be 60~70% for the first culturing, and to be 70~80% for the second culturing. In the atmosphere, carbon dioxide was maintained at a concentration of 3,000 ppm or less. Light was completely blocked for the culturing period of 30 days.

7. Mycelium Scraping

The number of sprouts was restrained by scraping gills to a distance of 15~20 mm.

8. Germination

Germination was carried out at 14-15° C. while the humidity was maintained at 90-95% for early germination of 3-5 days and at 70~80% for late germination of 3-5 days. In the atmosphere, carbon dioxide was maintained at a concentration of 1,000 ppm or less. Light was provided by a lamp in the daytime. The culture bottles were turned upside down for 5-8 days. When mushroom primodia grew about 1 cm in the later germination stage, the culture bottles were placed upright.

9. Breeding

To synchronize the sizes of young mushrooms formed at the mouth of the bottle, the temperature was set to be 11-12° C. and prevented from being elevated to 14° C. or higher. For the first three days, the temperature was maintained at 11° C. The culture condition was maintained to have a humidity of 70-95% so as to enlarge a difference in humidity between dry and wet states. After germination, the culture bottles were returned upright and incubated for 5-8 days. Immediately after returning upright, a low temperature was maintained so as to prevent a humidity change by dehumification.

10. Harvest

Mushrooms were harvested when the pilei still retained a hemispherical shape.

Figure 2:
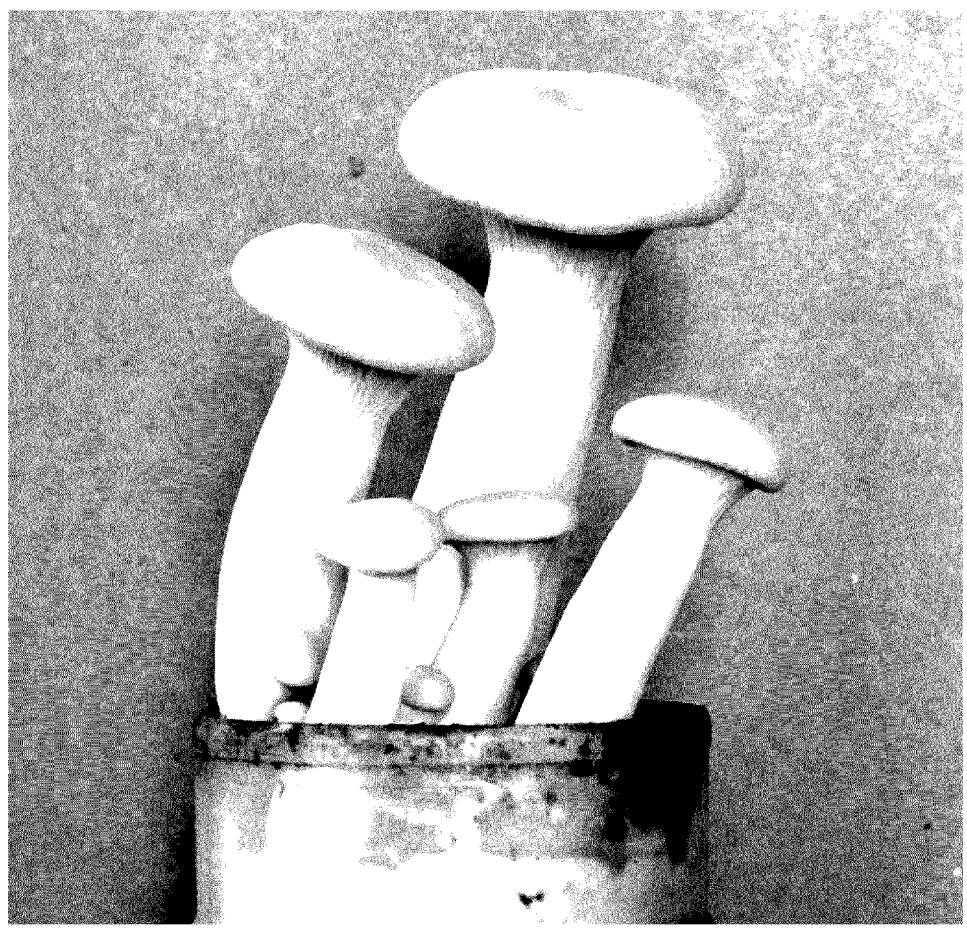
FIG. 2 is a photograph of fruit bodies of the novel *Pleurotus eryngii* var. *ferulae* strain P48-24s (accession No.: KCCM11288P) according to one embodiment of the present invention.

The novel *Pleurotus eryngii* var. *ferulae* strain P48-24s, and the P48-24S-lineage *Pleurotus eryngii* var. *ferulae* strains 1 to 5, obtained in the above Examples, were cultured and harvested. Although keeping the genetic features of DDL01 (KACC93085P), their fruit bodies were improved in pileus morphology and color, compared to the DDL01 (KACC93085P) strain of FIG. 1. The pileus was fully ivory white, without any other colors mixed therein, thus attracting consumer attention. As shown in FIG. 2, the fruit bodies of the novel strain P48-24s featured smooth and clean white pileus surfaces.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A novel *Pleurotus eryngii* var. *ferulae* strain representative inoculum having been deposited under Accession No.: KCCM11288P.

2. The novel *Pleurotus eryngii* var. *ferulae* strain P48-24s of claim 1, wherein when the novel strain is inoculated at regular intervals on a medium, no confrontation lines are formed between the inocula after replacement culture.

3. A fruit body of *Pleurotus eryngii* var. *ferulae*, produced by a novel *Pleurotus eryngii* var. *ferulae* strain P48-24s representative inoculum having been deposited under Accession No.: KCCM11288P.

4. The fruit body of claim 3, wherein the fruit body has a pileus surface that is fully ivory white, without any other colors mixed therein.

5. The fruit body of claim 3, wherein the fruit body has a bisporous basidium.

6. A mycelial culture of the novel *Pleurotus eryngii* var. *ferulae* strain P48-24s, representative inoculum having been deposited under Accession No.: KCCM11288P.

7. An inoculum, comprising the mycelial culture of claim 6.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Internal transcribed spacer 1

<400> SEQUENCE: 1
tccgtaggtg aacctgcgg                                                19

<210> SEQ ID NO 2
<211> LENGTH: 20
<212> TYPE: DNA
<213> ORGANISM: Artificial Sequence
<220> FEATURE:
<223> OTHER INFORMATION: Internal transcribed spacer 4

<400> SEQUENCE: 2
tcctccgctt attgatatgc                                               20

<210> SEQ ID NO 3
<211> LENGTH: 643
<212> TYPE: DNA
<213> ORGANISM: Pleurotus eryngii

<400> SEQUENCE: 3
ggaaggatca ttaatgaatt cactatggag ttgttgctgg cctctagggg catgtgcacg      60
cttcactagt ctttcaacca cctgtgaact tttgatagat ctgtgaagtc gtctctcaag     120
```

-continued

```
tcgttagact tggtttgctg ggatgtaaac gtctcggtgt gactacgcag tctatttact    180
tataacaccc caaatgtatg tctacgaatg tcatttaaag ggccttgtgc ctataaacca    240
taatacaact ttcaacaacg gatctcttgg ctctcgcatc gatgaagaac gcagcgaaat    300
gcgataagta atgtgaattg cagaattcag tgaatcatcg aatctttgaa cgcaccttgc    360
gccccttggt attccgaggg gcatgcctgt ttgagtgtca ttaaattctc aaactcactc    420
tggtttttcc aattgtgatg tttggattgt tgggggctgc tggccttgac aggtcggctc    480
ctcttaaatg cattagcagg acttctcatt gcctctgcgc atgatgtgat aattatcact    540
catcaatagc acgcatgaat agagtctggc tctctaaccg tccgcaagga caatttgaca    600
atttgacctc aaatcaggta ggactacccg ctgaacttaa gct                     643
```